United States Patent [19]
Ardito

[11] Patent Number: 5,140,999
[45] Date of Patent: Aug. 25, 1992

[54] URINARY INCONTINENCE VALVE DEVICE

[75] Inventor: James R. Ardito, Coon Rapids, Minn.

[73] Assignee: Primed International Corp., Coon Rapids, Minn.

[21] Appl. No.: 768,169

[22] Filed: Sep. 30, 1991

[51] Int. Cl.$^5$ .................... A61F 5/48; A61F 2/00; A61F 2/02

[52] U.S. Cl. .................... 128/885; 600/29; 600/30; 128/DIG. 25

[58] Field of Search ............ 128/842, 885, DIG. 25; 600/29–31; 623/11; 251/65

[56] References Cited

U.S. PATENT DOCUMENTS

| | | | |
|---|---|---|---|
| 3,731,670 | 5/1973 | Loe | 600/30 |
| 3,812,841 | 5/1974 | Isaacson | 600/29 |
| 3,926,175 | 12/1975 | Allen et al. | 128/DIG. 25 |
| 3,939,821 | 2/1976 | Roth | 600/30 |
| 4,013,063 | 3/1977 | Bucalo | 251/65 |
| 4,154,226 | 5/1979 | Hennig | 600/30 |
| 4,256,093 | 3/1981 | Helms | 600/31 |
| 4,453,536 | 6/1984 | Abild | 600/30 |
| 4,540,400 | 9/1985 | Hooven | 604/9 |
| 4,553,533 | 11/1985 | Leighton | 600/30 |
| 4,640,303 | 2/1987 | Greenberg | 251/65 |
| 4,679,546 | 7/1987 | Van Waalwijk van Doorn | 600/30 |
| 4,865,588 | 9/1989 | Flinchbaugh | 125/DIG. 25 |
| 5,004,454 | 4/1991 | Beyar | 600/30 |
| 5,030,199 | 7/1991 | Barwick | 600/29 |
| 5,041,092 | 8/1991 | Barwick | 600/29 |

Primary Examiner—Robert A. Hafer
Assistant Examiner—Michael Brown
Attorney, Agent, or Firm—Haugen and Nikolai

[57] ABSTRACT

A urinary incontinence valve for placement in the urethra of a male or female patient and which is magnetically-actuable from outside the body. The valve body is designed to fit into the neck of the bladder and includes an actuator rod which extends out of the valve body and into the bladder itself, providing greater freedom of movement of a valve surface relative to the valve seat. A compression spring normally urges the valve member to its closed position and when so closed, the compression spring is maintained in a urine-free environment.

17 Claims, 1 Drawing Sheet

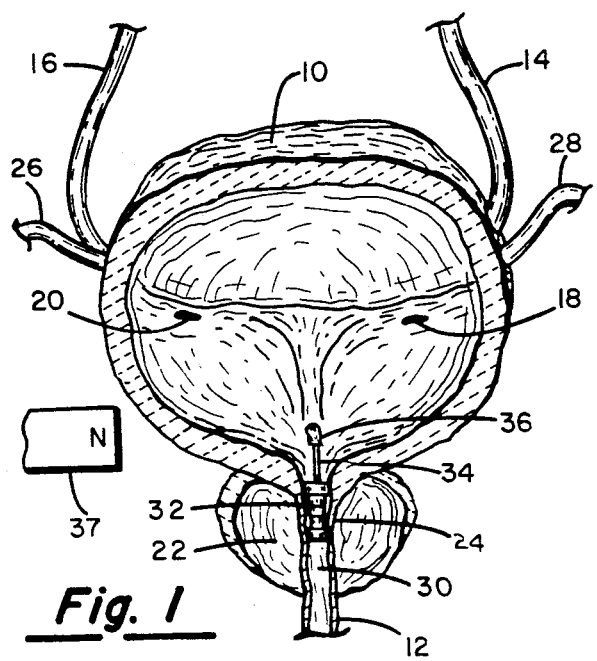
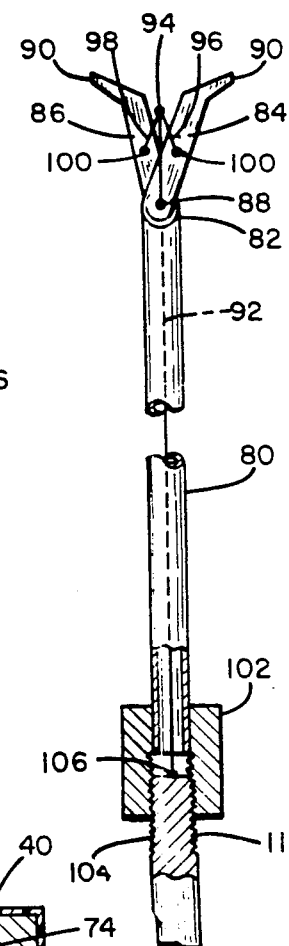
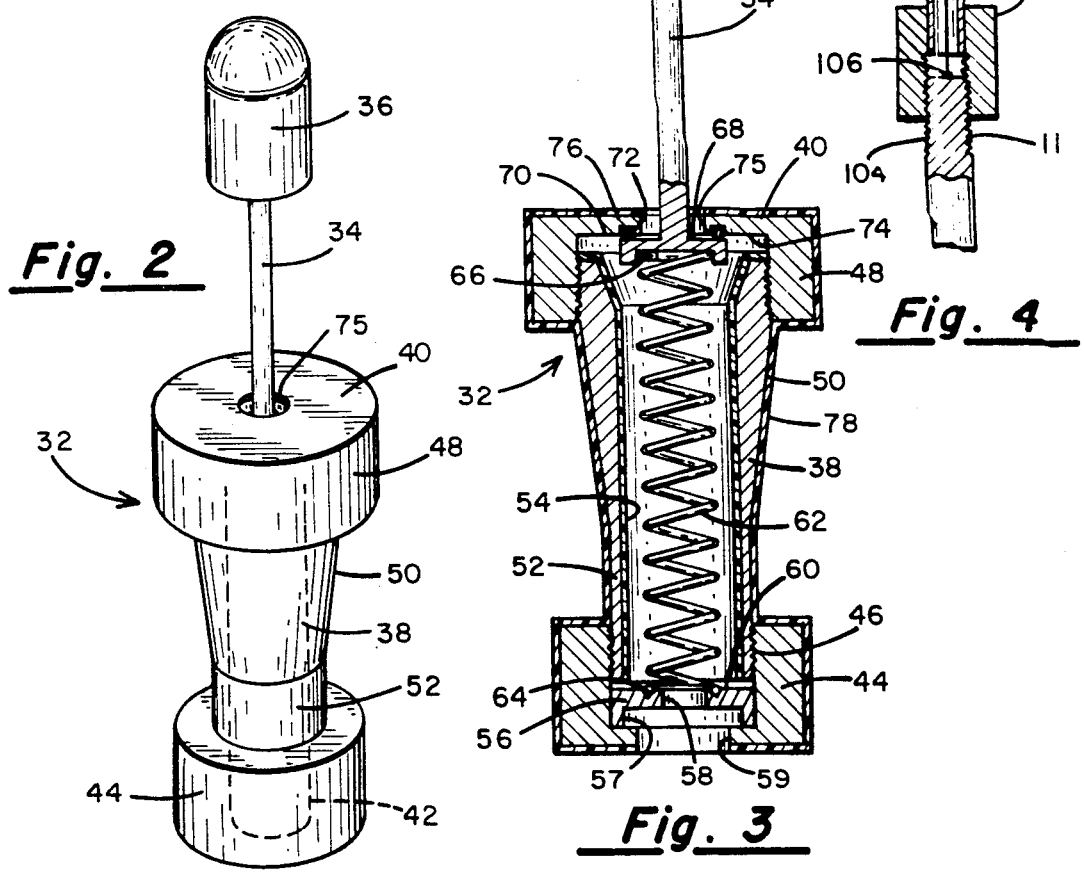
Fig. 1
Fig. 2
Fig. 3
Fig. 4

URINARY INCONTINENCE VALVE DEVICE

BACKGROUND OF THE INVENTION

I. Field of the Invention

This invention relates generally to medical apparatus, and more particularly to an implantable, magnetically-actuable valve mechanism which, when positioned in the urethra of a male or female patient, acts to selectively block urine flow, thus providing a treatment for urinary incontinence.

II. Discussion of the Prior Art

Urinary incontinence in both males and females remains a persistent problem, even though various methods and devices have been devised and proposed to treat the problem. The use of a catheter and associated collection bag with a clamping device on the catheter is useful only for relatively short-term situations. The presence of a long-term, indwelling catheter often leads to bladder infections in that the catheter provides a rather direct passage for bacteria or other microscopic organisms into the bladder. The use of special waterproof, water-retaining pants remains an option, but many who suffer urinary incontinence shy away from their use due to embarrassment and potential odor problems.

Another approach in treating urinary incontinence has involved the implantation of a valve into the urethra where the valve has a means operable external to the body to actuate it from a closed, urine-blocking position to an open, urine-draining position. In this regard, reference is made to the Isaacson U.S. Pat. No. 3,812,841 and the Beyar et al. U.S. Pat. No. 5,004,454. In each of these arrangements, the valve comprises a tubular body which may be inserted by an appropriate insertion stylet into the urethra. Contained within the valve body is a magnetically actuable valve member. When a permanent magnet is brought into proximity with the implanted valve, but exterior to the body, the valve may be shifted from its closed to its open position to allow the bladder to empty through the valve. Removal of the external magnet restores the valve to its urine-blocking disposition.

Each of the prior art magnetically-actuable, urinary incontinence valves described in the Isaacson '841 patent and the Beyar et al. '454 patent has design defects which render them unsuitable for their intended purpose. In particular, in each of the designs, a coil spring used to urge the valve against its valve seat is a tension-type spring which is continuously exposed to the bladder and, therefore, continuously bathed in urine. This can lead to valve failure when pitting of the metal of the spring occurs and when salt deposits build up on the spring element. Moreover, in the event of spring failure, it is possible for parts of the assembly to snap loose and be projected with force into the bladder. The device of the Beyar et al. patent also is deficient in that the valve orifice through which urine flows when the valve is actuated is quite small and the displacement of the valve surface from the valve seat is so small that urine flow is reduced to a trickle at best. The valve displacement from its seat is restricted by the fact that the cone-shaped valve member 21 can only be displaced very slightly by the external magnet because its movement is constrained by the walls defining the bore 12 of the valve body.

In each of these prior art designs, a stylet with a threaded distal end is used to engage the valve body either prior to insertion or at the time of removal. It is difficult, especially at the time of removal, to engage the threaded end of the stylet within the proximal end of the valve body when the valve body is in the urethra.

SUMMARY OF THE INVENTION

The present invention is somewhat similar in its mode of operation to the urinary incontinence valve of the prior art Beyar et al. patent in that it includes a tubular housing containing a spring which normally holds a valve surface in contact with a valve seat to block the flow of urine but which can be shifted to an open or urine-passing position by approaching the implanted device with a permanent magnet. It differs, however, in its constructional features in ways that obviate the aforementioned drawbacks of the prior art urinary incontinence valves. The urinary incontinence valve of the present invention is locatable within the urethra of the patient at a location proximate the exit of the urethra from the bladder. It comprises a tubular body member having a proximal end and a distal and an outer diameter sufficiently small to allow insertion of the valve assembly into the urethra of a patient and includes a lumen extending longitudinally from the proximal end to the distal end through which urine can flow. The valve body is of sufficiently short length that, when appropriately positioned in the urethra of a male patient, it does not block the ejaculatory ducts and inhibit seminal fluid flow.

A valve seat is disposed in the lumen of the body member proximate the distal end thereof. A movable valve member, having a valve surface cooperating with the valve seat, normally blocks liquid flow through the lumen of the valve body. A compression spring is disposed in the lumen of the valve body for normally urging the valve surface into sealing contact with its seat. An actuator rod is affixed to the valve member and projects outward of the lumen thereof at the distal end of the body member and is provided with a magnetizable member on its distal end. When a permanent magnet is brought into proximity of the magnetizable member on the actuator rod, the valve is tipped open relative to its seat, allowing the release and flow of urine through the valve body. Because the actuator rod extends exteriorly of the valve body and into the bladder, it is free to move a greater distance, thus providing greater displacement of the valve surface relative to its seat and permitting a more unrestricted flow of urine than can be achieved with the prior art valve devices, such as disclosed in the Beyar et al. patent, supra.

Moreover, because a compression spring rather than a tension spring is used and because it is placed proximal of the valve seat, it only becomes exposed to urine when the valve is actuated to its opened position. At all other times, it is sealed from exposure to urine, which decreases the frequency with which valve replacement must be made.

The force with which the valve surface is pressed against the valve seat is readily adjustable by means of a threaded nut secured to the proximal end of the valve body. This allows the valve to remain closed until actuated by a permanent magnet or until the head of urine within the bladder exerts a sufficient force on the valve to overcome the spring force and allow some limited drainage of the bladder even without the use of the external permanent magnet. This prevents backup of urine into the ureters and potential kidney damage.

The stylet used to insert and remove the urinary incontinence valve of the present invention from the body does not rely upon being able to mate a threaded end with corresponding threads on the valve body. Instead, it incorporates a scissors-like mechanism on the distal end of an elongated tube and a rotatable knob at the proximal end of that tube which is coupled to the scissors mechanism to cause it to open or close. When inserted into the proximal end of the valve body and opened, the valve body is securely coupled to the insertion stylet. Rotation of the knob so as to close the scissors mechanism decouples the stylet from the valve body.

DESCRIPTION OF THE DRAWINGS

The foregoing features, objects and advantages of the invention will become apparent to those skilled in the art from the following detailed description of a preferred embodiment, especially when considered in conjunction with the accompanying drawings in which:

FIG. 1 is a cross-sectional view taken through the bladder and a portion of the urethra of a male patient and showing the placement of the urinary incontinence valve of the present invention;

FIG. 2 is an enlarged perspective view of the preferred embodiment of the urinary incontinence valve of the present invention;

FIG. 3 is a longitudinal cross-sectional view taken through the urinary incontinence valve of FIG. 2; and FIG. 4 illustrates the insertion stylet used to install or later remove the valve.

DESCRIPTION OF THE PREFERRED EMBODIMENT

Referring to FIG. 1, there is shown a cross-sectional view taken through the urinary bladder 10 and the urethra 12 on a male patient. Tubular organs 14 and 16 are the right and left ureters which carry urine from the kidneys (not shown) through the ostia 18 and 20 into the interior of the bladder 10. The prostate gland is identified by numeral 22 and it surrounds the urethra 12. At a location indicated by numeral 24 is the external sphincter muscle which in normal patients constricts the urethra 12, preventing the passage of the urine there along. Due to trauma or disease, the sphincter 24 may lose its ability to constrict and release, leading to urinary incontinence, i.e., the uncontrolled flow of urine from the bladder through the urethra.

With continued reference to FIG. 1, the ampulla of vas deferens 26 and 28 come from the testicles and carry sperm which is ejected into the urethra via ejaculatory ducts 30 at the moment of sexual organism.

Shown positioned within the urethra and identified by numeral 32 is the urinary incontinence valve of the present invention. It is located in the one surrounded by the external sphincter 24 and because of the manner in which the exterior of the valve body is shaped, the sphincter 24 helps to anchor the valve against migration either into the bladder or down the urethra. The length of the valve body 32 is such that it does not interfere with or otherwise block the ejaculatory ducts 30 and, hence, does not inhibit normal sexual function. Associated with the valve body is a valve actuator 34 which extends out of the distal end of the valve body and into the interior of the bladder 10. Affixed to the distal end of the actuator rod 34 is a magnetizable member 36 which is preferably a ceramic magnet which is inert to body fluids, typically urine. As will be further explained, when a permanent magnet 37 is made to approach the pubic arch of the patient, it attracts the magnetizable member 36 and, via the actuator rod 34, to tip a valve member within the valve body 32 to its open position. The details of the construction of the urinary incontinence valve will be further described later in this specification.

FIG. 2 is an enlarged perspective view of the urinary incontinence valve 32. It is seen to comprise a valve body 38 which has a distal end 40 and a proximal end 42. A cylindrical nut 44 is secured to the proximal end portion of the valve body 38 by means of threads 46 (FIG. 3). As can be seen in FIGS. 2 and 3, the valve body 38 has an enlarged cylindrical, threaded cap 48 on its distal end and a conically tapered mid-section 50 which terminates in a generally cylindrical segment 52 leading to its proximal end 42. Because of the manner in which the external profile of the valve body 38 narrows, when the valve body is inserted into the urethra at the location of the external sphincter muscle, the sphincter muscles will grip the central portion of the valve body with migration in the distal direction being inhibited by the dimensions of the nut 44 and migration in the proximal direction prevented by the enlarged cap portion 48 of the valve body.

With continued reference to FIG. 3, the nut 44 includes a threaded bore 46 into which is fitted onto an annular washer 56 having a central opening 58 formed therein. The diameter of the opening 58 is slightly less than the internal diameter of the lumen 54 of the valve body and, as such, provides an inwardly projecting flange 60 against which the proximal end of a compression spring 62 rests. In particular, the upper surface of the flange 60 is provided with an annular groove 64 which captures the most proximal convolution of the compression spring 62 to hold the spring in position. The distal end of the spring 62 fits into a cavity 66 formed on the undersurface of a valve member 68 and normally urges the valve surface 70 into sealing relationship with respect to the valve seat 72. The valve seat 72 is formed in the undersurface 74 of the threaded cap surrounding the circular opening 75 of the cap 48. An elastomeric O-ring 76 fits into an annular groove formed on the undersurface of the valve seat 74 providing a water-tight seal with the movable valve member 68.

Integrally formed with the valve member 68 is the actuator rod 34. Threaded onto the distal end of the actuator rod 34 is the magnetizable member 36. As already mentioned, the actuator rod 34 positions the magnetizable member 36 into the bladder when the valve body 38 is positioned within the confines of the body's external sphincter muscle. By bringing permanent magnet sufficiently close to the magnetizable member 36, the member 36 will be attracted to the magnet and will cause the valve member 68 to tip relative to the O-ring seal 76 allowing urine to flow through the opening 75 formed in the threaded cap member 48 and then through the lumen 54 of the valve body 38 and thence through the central opening 58 of the washer 56 and through the urethra. When the permanent magnet is again removed, the spring 62 will restore the valve member 68 to its sealed position relative to the O-ring 76 of the valve seat 72.

The washer 56 includes a cylindrical, downwardly extending flange 57 which is supported on a shoulder 59 of the cylindrical nut 44 to create a chamber in the proximal end of the nut. As will be explained, this chamber accommodates a valve insertion/removal tool.

FIG. 4 illustrates the construction of the special stylet used during the installation or subsequent removal of the valve body from its location within the urethra. It is see to comprise an outer tubular member 80 whose outer diameter is sufficiently small to allow the instrument to be passed through the lumen of the urethra. It is generally rigid and may be formed from either stainless steel or a suitable plastic. Affixed to the distal end 82 of the tube 80 is a scissors-like mechanism having legs 84 and 86 pivotally joined at 88 to the tube 80. Each of the legs 84 and 86 has an angularly projecting foot 90. Extending longitudinally through the lumen of the tube 80 is an actuator rod 92 having a ring-like coupler 94 at its distal end. Linkages 96 and 98 extend between attachment points 100 on the blades 86 and 88 and the coupling ring 94.

Attached to the proximal end of the rod 80 is an internally threaded sleeve member 102 and screwed into the member 102 is a knob 104 whose surface is preferably knurled to facilitate being gripped between a thumb and forefinger. The rod 92 attaches to the knob 104 at tie-point 106.

As the knurled knob 104 is rotated in the clockwise direction, the actuator rod 92 moves in the distal direction and, operating through the linkages 96 and 98, causes the blades 84 and 86 to generally overlap one another. This reduces the distance between the ends of the feet 90, allowing those feet to be inserted through the opening 59 formed in the nut 44. Now, when the knob 104 is rotated in the counterclockwise direction, applying tension to the rod 92, the blades 84 and 86 will be caused to spread, locking the feet 90 within the spaced defined by the flange 57 of the washer 56. Once the valve is appropriately positioned within the urethra, the knob 104 can again be rotated in the clockwise direction, closing the blades 84 and 86 relative to one another and allowing the stylet to be removed from the opening within the proximal end of the valve body and out from the urethra. It should be readily apparent that if, later, it is desired to remove the valve from the body, the same stylet instrument of FIG. 4 may be employed.

The valve body 38 is preferably formed from stainless steel but may be formed from any number of suitable medical-grade plastic materials. When formed from stainless steel, it has been found desirable to coat the exterior thereof with a layer of a suitable elastomeric material, such as silicon rubber. This layer is identified by numeral 78 in FIG. 3. The exterior of the nut 44 and cap 48 is also coated with this silicon rubber for the purpose of providing an atraumatic surface relative to the tissue of the urethra. Likewise, it has been found expedient to coat the internal lumen 54 of the valve body with a film of a suitable polymeric material, such as polytetrafluoroethylene (Teflon).

Those skilled in the art can appreciate from the cross-sectional view of FIG. 3 the ease with which the parts comprising the urinary incontinence valve of the present invention can be assembled. The O-ring 76 is first inserted into the annular groove formed in the interior surface of the threaded cap. Next, the actuator rod 34 is dropped through the opening 75 of the cap. The cap can next be screwed onto the distal end of the valve body 38. The coil spring 62 may next be inserted into the proximal end of the valve body, followed by placement of the spacing washer 56 within the bore of the nut 44. The nut is then threaded onto the proximal end of the valve body which holds all of the parts in place. The assembly is completed by screwing the magnetizable member 36 onto the threaded end of the actuator rod 34. The compression force of the valve surface against its O-ring seat 76 can be adjusted by the extent to which the nut 44 is threaded onto its mating valve body.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A urinary incontinence valve disposable in the urethra of a patient for controlling the flow of urine therethrough comprising:
   (a) a tubular body member having a proximal end, a distal end and an outer diameter sufficiently small to allow insertion into the urethra of a patient and a lumen extending longitudinally from said proximal end to said distal end through which urine can flow;
   (b) a valve seat disposed in said lumen of said body member proximate said distal end;
   (c) a valve member including a valve surface cooperating with said valve seat for normally blocking liquid flow through said lumen;
   (d) an actuator rod affixed to said valve member projecting outward of said lumen at said distal end of said body member, said actuator rod including a magnetizable member attached to an end which is opposite an end extending into the lumen; and
   (e) stylet means for releasably gripping said proximal end of said tubular body.

2. The urinary incontinence valve as in claim 1 and further including a compression spring disposed in said lumen for normally urging said valve surface into sealing contact with said valve seat with a predetermined force.

3. The urinary incontinence valve as in claim 2 wherein said compression spring is disposed proximal of said valve surface.

4. The urinary incontinence valve as in claim 5 and further including means disposed at said proximal end of said body member for supporting said compression spring against said valve member.

5. The urinary incontinence valve as in claim 6 wherein said supporting means includes an annular plate disposed at said proximal end of said body member and a threaded nut affixed to said distal end of said body member.

6. The urinary incontinence valve as in claim 1 wherein said predetermined force is generally greater than the hydraulic force exerted on the valve member by the presence of a normal quantity of urine in the urinary bladder.

7. The urinary incontinence valve as in claim 1 wherein said actuator rod is of a sufficient length to position said magnetizable member within the bladder of the patient when said tubular body member is surrounded by the external sphincter of the patient.

8. The urinary incontinence valve as in claim 1 and further including a permanent magnet, which when disposed within a predetermined distance of said magnetizable member on said actuator rod and exterior to the body, displaces said valve surface relative to said valve seat.

9. The urinary incontinence valve as in claim 1 wherein the tubular body is made of stainless steel and includes an elastomeric coating on the exterior surface thereof and a compatible polymeric film coating on the wall surface defining said lumen.

10. The urinary incontinence valve as in claim 9 wherein said polymeric film coating is polytetrafluoroethylene and said elastomeric coating is selected from the group consisting of polyurethane, polyethylene and silicone rubber.

11. The urinary incontinence valve as in claim 1 wherein said stylet means comprises an elongated rigid tube having a proximal end, a distal end and a lumen extending therebetween; a scissors mechanism secured to said distal end of said rigid tube, said scissors mechanism capable of assuming a closed and an open position and means located at said proximal end of said rigid tube and affixed to said scissors mechanism for selectively urging said scissors mechanism to assume either said closed or said open position.

12. The urinary incontinence valve as in claim 11 wherein said scissors mechanism, when in said open position firmly engages said proximal end of said tubular body member and when in said closed position can be disengaged from said proximal end of said tubular body member.

13. A urinary incontinence valve for positioning in the urethra of a patient and controlling the flow of urine therethrough, comprising:

(a) a tubular body member having a proximal end, a distal end and an outer diameter sufficiently small to allow insertion into the urethra of a patient and a lumen extending longitudinally from said proximal end to said distal end through which urine can flow;

(b) a generally planar, annular valve seat surface disposed in said lumen of said body member proximate said distal end;

(c) a valve member having a generally planar valve surface cooperating with said planar valve seat surface for normally blocking urine flow through said lumen;

(d) an actuator rod affixed to said valve member so as to project outward from said distal end of said tubular body member into the urinary bladder of the patient when said body member is in the urethra, said actuator rod supporting a first permanent magnet outside said lumen; and (e) a second permanent magnet which when located exterior of the patient's body and proximate to said urinary incontinence valve, attracts said first permanent magnet to tip said actuator rod and said valve member relative to said valve seat surface, permitting urine flow through said annular valve seat surface and said lumen.

14. The urinary incontinence valve as in claim 13 and further including a compression spring disposed in said lumen for normally urging said generally planar valve member into sealing contact relative to said generally planar, annular valve seat surface with a predetermined force.

15. The urinary incontinence valve as in claim 14 wherein said compression spring is disposed proximal of said valve surface.

16. The urinary incontinence valve as in claim 13 wherein the length of said tubular body member is such that when said body member is surrounded by the patient's urinary sphincter, said valve body does not interfere with the ejaculatory ducts of the patient.

17. The urinary incontinence valve as in claim 13 wherein said tubular body is made of metal and is coated, as least in part, with polytetrafluoroethylene.

* * * * *

UNITED STATES PATENT AND TRADEMARK OFFICE
CERTIFICATE OF CORRECTION

PATENT NO. : 5,140,999
DATED : August 25, 1992
INVENTOR(S) : James R. Ardito It is certified that error appears in the above-identified patent and that said Letters Patent is hereby corrected as shown below:

Column 6, line 48, change "5" to -- 3 --.

Column 6, line 52, change "6" to -- 4 --.

Signed and Sealed this

Seventh Day of September, 1993

*Attest:*

BRUCE LEHMAN

*Attesting Officer*     *Commissioner of Patents and Trademarks*